United States Patent
Zhou et al.

(10) Patent No.: US 10,232,366 B2
(45) Date of Patent: Mar. 19, 2019

(54) METHOD FOR METERING A LIQUID IN AN ANALYTICAL DEVICE

(71) Applicant: Endress+Hauser Conducta GmbH+Co. KG, Gerlingen (DE)

(72) Inventors: Xu Zhou, Stuttgart (DE); Justyna Homa, Gerlingen (DE); Thomas Schipolowski, Stuttgart (DE); Thilo Krätschmer, Gerlingen (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 203 days.

(21) Appl. No.: 15/291,174

(22) Filed: Oct. 12, 2016

(65) Prior Publication Data

US 2017/0106363 A1    Apr. 20, 2017

(30) Foreign Application Priority Data

Oct. 16, 2015    (DE) .................. 10 2015 117 638

(51) Int. Cl.
    *B01L 3/00*      (2006.01)
    *G01N 1/28*      (2006.01)
    *G01N 33/18*     (2006.01)
    *G01F 11/00*     (2006.01)

(52) U.S. Cl.
    CPC .............. *B01L 3/502* (2013.01); *G01F 11/00* (2013.01); *G01N 1/28* (2013.01); *G01N 33/1806* (2013.01); *B01L 2200/0605* (2013.01); *B01L 2200/143* (2013.01)

(58) Field of Classification Search
    None
    See application file for complete search history.

(56) References Cited

U.S. PATENT DOCUMENTS

| 4,344,429 A | 8/1982 | Gupton et al. |
| 5,005,434 A | 4/1991 | Watanabe et al. |

FOREIGN PATENT DOCUMENTS

| DE | 3344848 C2 | 12/1991 |
| DE | 102012105379 B3 | 7/2013 |
| DE | 102013114138 A1 | 6/2015 |
| WO | 9733154 A1 | 9/1997 |
| WO | 2006013312 A1 | 2/2006 |

OTHER PUBLICATIONS

Search Report for German Patent Application No. 2015 117 638.6, German Patent Office, dated Oct. 28, 2015, 6 pp.

*Primary Examiner* — Xiaoyun R Xu
(74) *Attorney, Agent, or Firm* — Christopher R. Powers; PatServe

(57) ABSTRACT

The present disclosure relates to a method for metering a liquid into a wet chemistry analytical device wherein a specified volume of individual liquids is placed in a metering unit consisting of a metering container and at least one dose measuring device. During the filling of the metering container with the respective liquid, after the activation of the dose measuring device, an additional volume of the liquid is drawn into the metering tube beyond the position of the dose measuring device, wherein during this procedure and afterwards the status of the dose measuring device is checked, and a conclusion is drawn from this regarding the presence of an air bubble-free liquid in the metering tube.

18 Claims, 2 Drawing Sheets

METHOD FOR METERING A LIQUID IN AN ANALYTICAL DEVICE

CROSS-REFERENCE TO RELATED APPLICATIONS

The present application is related to and claims the priority benefit of German Patent Application No. 10 2015 117 638.6, filed on Oct. 16, 2015, the entire contents of which are incorporated herein by reference.

TECHNICAL FIELD

The present disclosure relates to methods of metering a liquid, in particular metering liquids in wet chemistry.

BACKGROUND

From DE 10 2013 114 138 A1, an analytical device is known for determination of a digestion parameter of a liquid sample, comprising at least one reactor and measuring device for determining the parameter of the liquid sample, a container device for storage of samples, reagents, and waste products in containers, a feed and metering device for metering and feeding the sample and reagents from the containers into a metering vessel and for disposal of waste products from the metering vessel into a waste container, and a sensing element for detecting a measured value, correlating with the parameter to be measured, of the liquid sample optionally mixed with one or more reagents in the reactor and measuring device. The feed and metering device consists at least of a metering vessel, a piston pump, and an additional sample collection device for at least taking a sample of a given volume of a liquid as a liquid sample from a sample collection site.

During the metering of the liquids, accurate determination of the volume of the liquids is of great significance. During metering, the respective liquid is drawn at high speed in the direction of the dose measuring device, until the metering unit activates. The liquid located in the metering unit is then forced at reduced speed below the dose measuring device. Then, the missing liquid is drawn in at low speed up to the dose measuring device.

Both during purging and during accurate metering for the measurement process, the dose measuring device may be activated not only by the liquid, but also by a liquid film surrounding an air bubble or by liquid films in the metering unit that form due to air bubbles. These air bubbles form whenever the liquid-carrying tubes are not completely filled with liquid or when the liquids or reaction products outgas. This is especially critical during the purging of the sample, since the sample tubing is empty before each measurement.

During the purging of the analytical device, these air bubbles can cause the metering device to not be completely rinsed and/or the measurement reactor to not be completely emptied. Because of the high feed velocity and the possibly high suction breadth or pressure, there is a risk that air bubbles will be drawn into the metering unit and erroneously activate the dose measuring device because of the film of liquid surrounding the air bubble or the liquid film formed in the metering device by the air bubbles.

In a measurement process, erroneous activation of the dose measuring device can lead to the volume to be metered not being set correctly. This will impair the measurement accuracy of the analytical device. Accordingly, there remains a need for further contributions in this area of technology for metering liquids.

BRIEF SUMMARY

The present disclosure is based upon the aim of specifying a method for metering a liquid in which the required volume of the liquid is precisely set, even if air bubbles are drawn in together with the liquid. The present disclosure relates to a method for metering a liquid into a wet chemistry analytical device for determining a parameter of a liquid sample, in which a measurement reactor is filled with liquids, preferably with the liquid sample and several reagents or standards required for analysis, wherein, before the measurement reactor is filled, a specified volume of the individual liquids is placed in a metering unit consisting of a metering container and at least one dose measuring device.

According to at least one embodiment of the present disclosure, the aim is achieved in that, during the filling of the metering container, designed as a metering tube, with the respective liquid, after the activation of the dose measuring device, an additional volume of the liquid is drawn into the metering tube beyond the position of the dose measuring device, wherein, during this procedure and afterwards, the status of the dose measuring device is checked, and a conclusion is drawn from this status check regarding the presence of an air bubble-free liquid in the metering tube. In this way, it is possible to recognize whether an air bubble or a liquid film is present in the metering tube.

Advantageously, an air bubble-free liquid is present in the metering tube, when the dose measuring device, before and after filling the additional volume, is not yet activated. In this way, the measuring process can be continued after precisely setting the desired volume of liquid.

In one embodiment, the presence of an air bubble or liquid film is inferred when the dose measuring device is activated during filling of the metering tube if, during and after addition of the additional volume, the dose measuring device changes from the activated state to the non-activated state. If an air bubble or a liquid film is detected, the filling process of the metering tube is continued until the dose measuring device is activated again. Then, another additional volume is drawn in, and the status of the dose measuring device is again checked, since the liquid may also contain several air bubbles separated from one another by liquid films. The process is repeated until no further air bubble or liquid film is recognized. After the desired volume of liquid has been set precisely, the measuring process is continued.

In another embodiment, after detection of an air bubble or a liquid film, more liquid is added to the liquid already present in the metering tube until the dose measuring device has been activated, wherein, after the activation of the dose measuring device, the additional liquid volume is drawn in to check the status of the dose measuring device. This process is repeated until the status of the dose measuring device clearly shows that no air bubble or liquid film is present in the liquid.

In one variant, a first drawing of the liquid takes place into an empty metering tube. In this process, it is assumed that the metering tube is filled only with air.

In a further embodiment, the additional volume amounts to less than 5% of the volume of the liquid to be set. Thus, a small amount of additional volume is sufficient to check the liquid for the presence of air bubbles.

BRIEF DESCRIPTION OF THE DRAWINGS

The present disclosure allows numerous embodiments, which will be described in further detail with reference to the figures that are depicted in the drawings.

In the figures, the same features are marked with the same reference symbols.

DETAILED DESCRIPTION OF THE DRAWINGS

Figure 1:
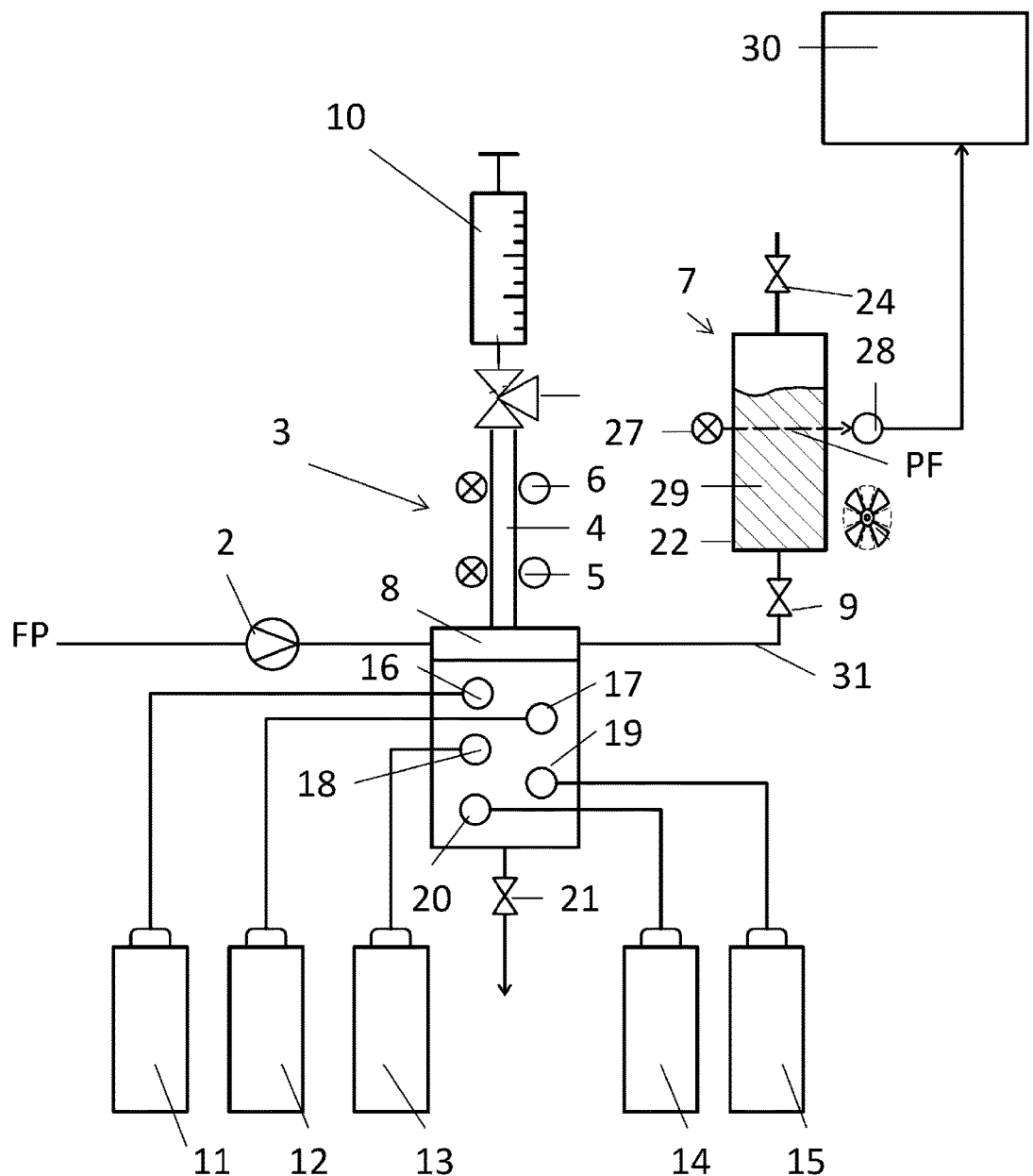
FIG. 1 shows an embodiment of an analytical device according to the present disclosure.

In FIG. 1, an embodiment of an analytical device 1 used for determining digestion parameters in liquid samples, preferably in process measurement technology or in industrial measurement technology, is shown. Such digestion parameters are used, for example, in the area of water and wastewater treatment and/or in water and wastewater analysis. Examples of digestion parameters are chemical oxygen demand, total carbon content, total nitrogen content, and total phosphorus content.

The chemical oxygen demand (COD) is the quantity of chemically oxidizable substances in a water sample, expressed as the oxygen equivalent. This parameter can be advantageously determined with the analytical device 1 shown in FIG. 1. For determining the chemical oxygen demand, a liquid sample FP is fed through a peristaltic pump 2 into a metering unit 3. In this example, the liquid sample FP can be taken from an open basin or a closed container. The liquid sample FP can, for example, be wastewater in a wastewater treatment plant.

In the metering unit 3, which consists of a metering tube 4 and two dose measuring devices 5, 6, e.g., light barriers, the volume of the liquid sample FP to be analyzed is determined. The dose measuring device 5 activates (i.e., triggers) when this volume is reached, ending the filling of the metering unit 3. The liquid sample FP is then delivered from the metering unit 3 into the measurement reactor 7. This takes place via a valve block 8 and an opened reactor inlet valve 9. The metering device 6 serves solely as a back-up measuring device.

At one end of the metering unit 3, adjacent to the valve block 8, a piston pump 10 is arranged, by means of which reagents or standards are individually drawn into the metering unit 3. These reagents are solutions that must be added to the liquid sample FP for determination of the chemical oxygen demand COD, whereas the standards are used for calibration and/or adjustment of the analytical device 1.

The reagents, along with a calibration standard and a blank, are individually placed in liquid containers 11, 12, 13, 14, 15, which are connected via the valve block 8 with the metering unit 3, wherein, within the valve block 8, each liquid container 11, 12, 13, 14, 15 is assigned to a valve 16, 17, 18, 19, 20, which is opened to fill the metering unit 3 with a liquid contained in one of the liquid containers 11, 12, 13, 14, 15 and closed again after the metering unit 3 is again filled. In addition, a valve 21 is arranged beneath or downstream of the valve block 8, which allows for waste disposal of the mixture from the measurement reactor 7 after the measurement is complete.

The first liquid container 11 contains as the digestion agent an aqueous potassium dichromate solution, whereas the second liquid container 12 contains an aqueous mercury sulfate solution for masking any chloride ions contained in the liquid, and the third liquid container 13 contains a sulfuric acid with silver sulfate as catalyst. The fourth liquid container 14 contains a calibration standard. This is a standard solution that has a preset first chemical oxygen demand. In another liquid container 15 is a second standard solution with a second chemical oxygen demand different from the first chemical oxygen demand, e.g., deionized water, which is used as the null standard.

The measurement reactor 7 includes a digestion vessel 22 made of an optically transparent material, e.g., glass, which can be heated by a heating device—not presented in further detail—before and during the measurement process. In this digestion vessel 22 of the measurement reactor 7, by way of the reactor inlet valve 9, flows a liquid line 31 optionally connectable with the metering unit 3 or with a waste container, not shown in further detail. At the end of the measurement reactor 7 opposite the reactor inlet valve 9, a reactor pressure compensation valve 24 is located.

The measurement reactor 7 for determining the measured value representing the chemical oxygen demand of the liquid sample FP includes a photometric sensor having a light source 27 and a photoreceiver 28. The light source 27 can, for example, comprise one or more multicolor LEDs, especially ones emitting light of different wavelengths, and the photoreceiver 28 can have one or more photodiodes. Light emitted by the light source 27 passes through the measurement reactor 7 along a measurement path PF traveling through the reaction mixture 29 contained in the digestion vessel 22 and strikes the photoreceiver 28, which is connected to an evaluation unit 30. In this way, a light source 27 is selected which emits a wavelength, the absorption or extinction of which is a measure of the consumption of the digestion agent in the form of potassium dichromate, serving for oxidation of oxidizable components of the liquid sample FP.

The photometric sensor 27, 28 emits an electrical measurement signal dependent upon the intensity of the light striking the photoreceiver 28. The light intensity striking the photoreceiver 28 depends upon the extinction or absorption of the reaction mixture 29 contained in the measurement reactor 7. Thus, the electrical measurement signal emitted by the photometric sensor 27, 28 is a measure of the chemical oxygen demand COD of the liquid sample FP.

Figure 2:
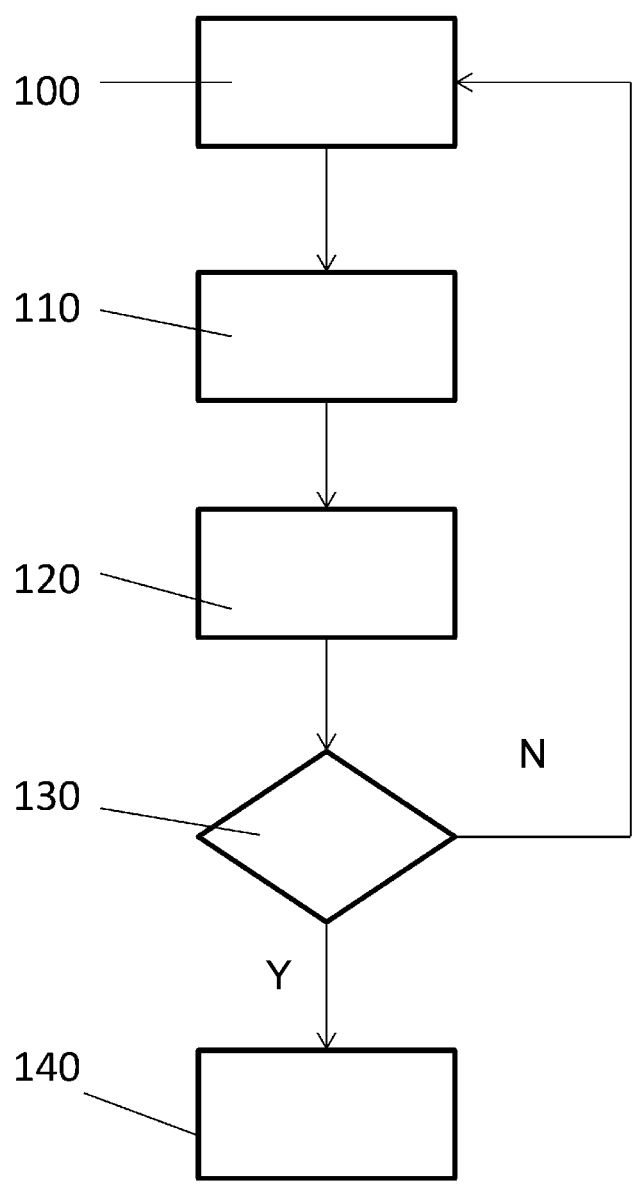
FIG. 2 shows an embodiment of a method according to the present disclosure.

In the embodiment according to FIG. 2 of the method according to the present disclosure, in the first step 100, the liquid is filled at a high rate of speed by means of the piston pump 10 or the peristaltic pump 2 into the empty metering tube 4 until this reaches the dose measurement device 5. After the dose measurement device 5 has activated after filling of the liquid in step 110, and the desired volume has thus been established, the method includes a step 120 in which an additional volume of the liquid, above the level of the dose measurement device 5, is drawn into the metering tube 4. In step 130, a check is made to see whether the dose measuring device 5 is still activated. If the status of the dose measuring device 5 has not changed, and if this is still interrupted, the absence of air bubbles in the liquid is ensured. In step 140, the volume of the liquid is forced below the level of the dose measuring device 5 (i.e., the excess volume exceeding the desired volume) and drawn into the level of the dose measuring device 5, and the liquid measured in this way is introduced into the measurement reactor 7 for analysis.

If, however, it is determined in step 130 that the status of the dose measuring device 5 has changed, and this is no longer activated, it is assumed that the first activation of the dose measuring device 5 was caused by an air bubble or a liquid film. The process is returned to step 100, in which the liquid is drawn into the dose measuring device. Then, the additional volume is added in step 110.

By checking the content of the metering tube 4 with the additional volume, the filling of the metering tube 4 with liquid up to the dose measuring device 5 is ensured. In this way, incorrect dosing during the measurement operation of the analytical device or entrainment due to inadequate rinsing during purging of the analytical device are reliably prevented.

The invention claimed is:

1. A method for metering a liquid in an analytical device comprising:
   introducing a first volume of a first liquid into a metering container of a measuring unit, the measuring unit including a dose measuring device disposed adjacent the metering container, wherein the first liquid is introduced into the metering container until the dose measuring device is triggered, the dose measuring device including at least one light barrier configured to be triggered by an air-liquid transition;
   adding an additional volume of the first liquid into the metering container after the dose measuring device is triggered;
   during and after adding the additional volume, determining a status of the dose measuring device as to whether the dose measuring device is triggered; and
   operating on the status of the dose measuring device to determine whether the first liquid includes a bubble or film.

2. The method according to claim 1, wherein the first liquid in the metering container is determined to be bubble-free and film-free when the dose measuring device remains triggered during and after adding the additional volume.

3. The method according to claim 2, the method further comprising:
   purging an excess volume of the first liquid from the metering container until a level of the first liquid in the measuring container is at or near the dose measuring device to yield a desired volume of the first liquid, wherein the excess volume is defined as a sum of the first volume and the added additional volume less the desire volume; and
   introducing the desired volume into a measurement reactor configured for analysis.

4. The method according to claim 1, wherein the first liquid in the metering container is determined to include a bubble or a film when, after triggering the dose measuring device during the introducing of the first liquid into the metering container, the status of the dose measuring device changes from triggered to not triggered during or after the introduction of the additional volume.

5. The method according to claim 4, the method further comprising:
   after determining that the first liquid includes a bubble or a film, repeating the adding of the additional volume until the dose measuring device is subsequently triggered;
   after the subsequent triggering of the dose measuring device, repeating the adding of the additional volume;
   during and after the repeated adding of the additional volume, determining a status of the dose measuring device as to whether the dose measuring device is triggered; and
   operating on the status of the dose measuring device to determine whether the first liquid includes a bubble or film.

6. The method according to claim 1, wherein the first liquid in the metering container is determined to include a bubble when, after triggering of the dose measuring device during the introducing of the first liquid into the metering container, the status of the dose measuring device changes from triggered to not triggered during and after the introduction of the additional volume.

7. The method according to claim 1, wherein before the introducing of the first liquid into the metering container, the metering container is empty.

8. The method according to claim 1, wherein the additional volume is less than 5% of a desired volume of the first liquid.

9. The method according to claim 3, the method further comprising:
   repeating the method with a second liquid.

10. The method according to claim 9, wherein the first liquid and/or the second liquid is/are a liquid sample, a reagent or a standard.

11. The method according to claim 1, wherein the metering container is a metering tube.

12. The method according to claim 1, wherein the first volume of the first liquid introduced before the additional volume is a desired volume.

13. A method for metering a liquid in a wet chemistry analytical device for determining a parameter of a liquid sample, in which a measurement reactor is filled with liquids, such as a liquid sample and several reagents or standards required for analysis, wherein before the measurement reactor is filled, a respective specified volume of the individual liquids is placed in a metering unit including a metering container and at least one dose measuring device, the method comprising, during the filling of the metering container with the respective specified volumes, which triggers the dose measuring device, an additional volume of the individual liquids is drawn into the metering container beyond a position of the dose measuring device, wherein, during the drawing of the additional volume and afterwards, a status of the dose measuring device is checked, and a conclusion is drawn from the status regarding the presence of an air bubble-free liquid in the metering container.

14. The method according to claim 13, wherein the liquid in the metering container is determined to be air bubble-free and film-free when the dose measuring device remains triggered during and after drawing the additional volume.

15. The method according to claim 13, the method further comprising:
   purging an excess volume of the liquid from the metering container until a level of the liquid in the measuring container is at or near the position of the dose measuring device to yield a desired volume of the liquid, wherein the excess volume is defined as a sum of the respective specified volumes and the added additional volume less the desire volume; and
   introducing the desired volume into the measurement reactor configured for analysis.

16. The method according to claim 13, wherein the liquid in the metering container is determined to include a bubble or a film when, after triggering the dose measuring device during the filling of the metering container, the status of the dose measuring device changes from triggered to not triggered during or after the drawing of the additional volume.

17. The method according to claim 16, the method further comprising:

after determining that the liquid includes a bubble or a film, repeating the adding of the additional volume until the dose measuring device is subsequently triggered;

after the subsequent triggering of the dose measuring device, repeating the adding of the additional volume;

during and after the repeated adding of the additional volume, determining a current status of the dose measuring device as to whether the dose measuring device is triggered; and operating on the current status of the dose measuring device to determine whether the liquid includes a bubble or film.

18. The method according to claim 13, wherein the liquid in the metering container is determined to include a bubble when, after triggering of the dose measuring device during the filling the metering container with the liquid, the status of the dose measuring device changes from triggered to not triggered during and after the drawing of the additional volume.

* * * * *